United States Patent
Zhang

(10) Patent No.: US 9,265,872 B2
(45) Date of Patent: Feb. 23, 2016

(54) DEVICE AND METHOD FOR MEASURING A BLOOD CONSTITUENT IN BLOOD FOR AN EXTRACORPOREAL BLOOD TREATING DEVICE

(75) Inventor: Wei Zhang, Niederwerrn (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 1055 days.

(21) Appl. No.: 13/263,450

(22) PCT Filed: Apr. 8, 2010

(86) PCT No.: PCT/EP2010/002188
§ 371 (c)(1),
(2), (4) Date: Oct. 7, 2011

(87) PCT Pub. No.: WO2010/115621
PCT Pub. Date: Oct. 14, 2010

(65) Prior Publication Data
US 2012/0031841 A1    Feb. 9, 2012

(30) Foreign Application Priority Data
Apr. 11, 2009   (DE) .................. 10 2009 017 304

(51) Int. Cl.
| B01D 11/00 | (2006.01) |
| B01D 61/00 | (2006.01) |
| C02F 1/44 | (2006.01) |
| A61M 1/16 | (2006.01) |
| A61B 5/1455 | (2006.01) |

(Continued)

(52) U.S. Cl.
CPC .............. *A61M 1/16* (2013.01); *A61B 5/14557* (2013.01); *A61M 1/361* (2014.02); *A61B 5/14532* (2013.01); *A61M 2230/30* (2013.01)

(58) Field of Classification Search
USPC .......................... 210/85, 93; 356/39
See application file for complete search history.

(56) References Cited

U.S. PATENT DOCUMENTS

| 5,312,550 A | 5/1994 | Hester |
| 5,529,685 A * | 6/1996 | Irie et al. ................. 210/134 |
| 6,222,189 B1 | 4/2001 | Misner et al. |
| 6,493,567 B1 | 12/2002 | Krivitski et al. |
| 6,587,704 B1 | 7/2003 | Fine et al. |
| 6,666,840 B1 | 12/2003 | Falkvall et al. |
| 7,420,658 B2 | 9/2008 | Petterson et al. |
| 2004/0129616 A1 | 7/2004 | Mori et al. |

(Continued)

FOREIGN PATENT DOCUMENTS

| DE | 199 11 265 A1 | 9/2000 |
| DE | 603 12 737 | 12/2007 |

(Continued)

OTHER PUBLICATIONS

International Search Report for PCT/EP2010/002188, mailed on Oct. 6, 2010.

(Continued)

*Primary Examiner* — Dirk Bass
(74) *Attorney, Agent, or Firm* — Kenyon & Kenyon LLP

(57) ABSTRACT

The invention relates to a device and a method for measuring a blood constituent in blood for an extracorporeal blood treatment device, comprising a dialyzer or a filter, and a hose line system comprising hose lines that are pervious to electromagnetic radiation. The kinetics of a liquid flowing at a measuring site in one of the hose lines of the hose line system is varied by varying the flow properties of the liquid in the hose line at the measuring site, particularly by stopping a blood pump arranged in the hose line and/or by closing a shut-off member in the hose line. The invention analyzes the intensity of the light entering the hose line at the measuring site and the light exiting the hose line at the measuring site.

21 Claims, 4 Drawing Sheets

(51) Int. Cl.
*A61M 1/36* (2006.01)
*A61B 5/145* (2006.01)

(56) References Cited

U.S. PATENT DOCUMENTS

2005/0243303 A1* 11/2005 Pettersson et al. ............. 356/39
2007/0083145 A1   4/2007 Murakami et al.

FOREIGN PATENT DOCUMENTS

| EP | 1083948 B1 | 3/2001 |
|---|---|---|
| JP | 09-500721 A | 1/1997 |
| WO | 94/27495 A1 | 12/1994 |
| WO | 2004/057313 A1 | 7/2004 |
| WO | 2004/105596 A1 | 12/2004 |
| WO | 2006/006153 A1 | 1/2006 |
| WO | 2007/020647 A1 | 2/2007 |
| WO | 2007/140993 A1 | 12/2007 |

OTHER PUBLICATIONS

"Occlusion Spectroscopy as a New Paradigm for Non-Invasive Blood Measurement," Ilya Fine et al., Proceedings of SPIE, vol. 4263, pp. 122-130, 2001.

* cited by examiner

DEVICE AND METHOD FOR MEASURING A BLOOD CONSTITUENT IN BLOOD FOR AN EXTRACORPOREAL BLOOD TREATING DEVICE

CROSS REFERENCE TO RELATED APPLICATIONS

This is a 371 national phase application of PCT/EP2010/002188 filed Apr. 8, 2010, claiming priority to German Patent Application No. 10 2009 017 304.8 filed Apr. 11, 2009.

FIELD OF INVENTION

The present invention relates to an arrangement and method for measuring a blood constituent in blood, for an extra-corporeal blood treating apparatus which comprises a dialyzer or filter, which is divided by a semi-permeable membrane into a first chamber and a second chamber, and a system of flexible lines, which are transmissive of electromagnetic radiation,

BACKGROUND OF THE INVENTION

In cases of chronic kidney failure, various methods of extra-corporeal blood treatment or cleansing are used to remove substances that need to be excreted and to withdraw fluids. In hemodialysis, the patient's blood is cleaned outside the body in a dialyzer. The dialyzer has a blood chamber and a dialysis-fluid chamber which are separated by a semi-permeable membrane. During the treatment the patient's blood flows through the blood chamber. To allow the blood to be cleansed effectively of substances that need to be excreted, there is a continuous flow of fresh dialysis fluid through the dialysis-fluid chamber.

Whereas in hemodialysis (HD) the transport of low-molecular substances through the membrane of the dialyzer is determined in essence by the differences in concentration between the dialysis fluid and the blood (diffusion), in hemofiltration (HF) substances dissolved in the water of the plasma, and in particular substances of fairly high molecular weight, are effectively removed by a high flow of fluid through the membrane of the dialyzer (convection). A combination of the two methods is called hemodiafiltration (HDF).

In dialysis patients, what often occur in addition to kidney failure are accompanying conditions, one of which, in a third of all cases, is diabetes mellitus. To minimize any further damaging sequelae, it is necessary for the therapy for the diabetes to be optimally adjusted. Diagnosis of diabetes mellitus and the monitoring of the therapy are performed by measuring blood sugar (blood glucose).

Both invasive and non-invasive methods of measuring blood glucose are known. Known non-invasive methods of determining blood glucose are based on measurement of the transmission of light in the patient's blood. In the infrared region, the absorption bands of glucose are at 760 nm, 920 nm and 1000 nm. However, the absorptions are so small as to be scarcely detectable. Use is therefore made of what is referred to as artificial blood kinetics.

What is used in the known non-invasive methods to measure the concentration of glucose in the patient's blood is a measuring set-up that has a pressure cuff that is applied to the patient's finger, the pressure cuff having a light source, and optical sensors for measuring transmission. A pressure that is above the systolic pressure is applied briefly to the pressure cuff on the patient's finger and the flow of blood in the finger is thus stopped, by which means what are referred to as artificial blood kinetics are produced. The red blood corpuscles collect together in groups and there is thus an increase in the size of the scattering bodies. It is possible in this way for the concentration of glucose in the blood to be determined on the basis of a measurement of transmission.

The known methods of measurement make provision for the individual measured results to be analyzed in different ways. However, what all the methods of measurement have in common is that a measurement of transmission is made at the patient's finger while pressure is being applied to the patient's finger with a pressure cuff to produce artificial blood kinetics.

The methods described above of measuring the concentration of glucose in blood are described in detail in for example the article entitled "Ilya Fine, et al: Occlusion Spectroscopy as a New Paradigm for Non-Invasive Blood Measurement, Proceedings of SPIE, Vol. 4263, pp. 122-130, 2001". The known methods of measurement for measuring glucose concentration are also described in detail in WO 2006/006153 A1, WO 2007/020647 A1 and WO 2004/105596 A1.

WO 2004/105596 A1 describes a method of measuring glucose concentration in which the blood flow in a finger is stopped by a first pressure cuff and the blood flow in the fingertip is modulated by a second pressure cuff which is arranged between the first cuff and the fingertip. Artificial blood kinetics are produced by this means in the fingertip and these effect the measurement of transmission and are used to allow the hemoglobin value to be calculated.

A method of determining the concentration of glucose in a dialysis fluid during a dialysis treatment is known from EP 1 083 948 B1. However, it is a precondition of this known method that a sample of dialysis fluid be taken during the dialysis treatment.

The known methods of measuring glucose have proved successful in practice. However, it is a disadvantage that a pressure cuff has to be fitted to the patient's finger or that a sample has to be taken.

SUMMARY OF THE INVENTION

The object underlying the present invention is to provide an arrangement by which non-invasive measurement of a blood constituent, such for example as the concentration of glucose in the blood, is possible during extra-corporeal blood treatment by means of a blood treating apparatus. The object underlying the present invention is also to specify a method for the non-invasive measurement of a blood constituent in the blood during extra-corporeal blood treatment by means of a blood treating apparatus.

The arrangement according to the present invention and the method according to the present invention make use of the fact that the systems of flexible lines that are used in the known pieces of blood treating apparatus are generally flexible lines which transmit electromagnetic radiation, and in particular light. The present invention is based on changing the kinetics of the fluid which is flowing at a point of measurement in at least one flexible line of the system of flexible lines. This can be done by changing the hydrodynamic behavior of the fluid in the at least one flexible line of the system of flexible lines at the point of measurement. The actual analysis of the measurement data obtained, for the purpose of determining the concentration of the blood constituent, is then performed by the known methods which make use of a cuff on the patient's finger, but what the invention analyzes in this case is the intensity at various wavelengths of the electromagnetic radiation which enters the flexible line at the point of measurement and which emerges from the flexible line at the point of measurement. The change in the hydrodynamic behavior of the fluid flowing in the flexible line results in the blood constituent being able to be determined by a measurement of transmission, reflection and scattered light.

Except for the measuring set-up, the arrangement according to the present invention and the method according to the invention are able to make use of the components which are already present in the known pieces of extra-corporeal blood treating apparatus. These include for example the central control and computing unit, by which the settings required for the Measurement can be made and the analysis of the measurement data obtained can be performed. The crucial advantage of the arrangement according to the present invention and the method according to the invention is that non-invasive measurement of the blood constituent is possible before or after or during the extra-corporeal blood treatment, but without a pressure cuff having to be fitted to the patient's finger or a sample of dialysis fluid having to be taken.

Extra-corporeal blood treatment makes continuous access possible to the patient's blood. Various constituents of the blood, such as glucose for example, are able to pass through the dialyzer or filter of an extra-corporeal blood treating apparatus, and because of this the measurement can, fundamentally, take place both in the extra-corporeal blood circuit and in the dialysis-fluid circuit. Preferably however the measurement is made in at least one flexible line of the system of flexible lines in the extra-corporeal blood circuit, and in particular in the inlet line for blood which runs to the blood chamber of the dialyzer or filter of the blood treating apparatus.

The hydrodynamic behavior of the fluid flowing in at least one flexible line of the extra-corporeal blood circuit can be changed in different ways. In an embodiment of the invention which is a particular preference, provision is made for the hydrodynamic behavior of the blood flowing in the blood inlet line or blood return line to be changed by changing the pumping rate of the blood pump which is arranged in the extra-corporeal blood circuit, and in particular in the blood inlet line. The blood pump is preferably stopped for a brief interval of time, such for example as for 2 to 20 seconds, and in particular for 8-12 seconds. The blood pump need not be completely stopped however and the blood flow may only be abruptly reduced. Basically, it is also possible for the pumping rate of the blood pump to be changed briefly, and in particular to be raised and reduced briefly, in order to change the hydrodynamic behavior. The blood flow may for example be raised from 250 ml/min to 400 ml/min and then reduced to 100 ml/min before the blood flow of 250 ml/min is again set.

In a further embodiment which is a particular preference, both the blood pump is stopped for a preset brief interval of time and a shut-off member, such for example as a tube clamp, which is arranged in the extra-corporeal blood circuit and in particular in the blood inlet line at a point upstream of the blood pump, is also closed, the measurement being performed in the portion of the flexible line which is upstream of the shut-off member. The shut-off member is then opened again and the blood pump put back into operation. It is also possible for the shut-off member to be opened and closed more than once to make the artificial change in the blood kinetics. The shut-off member is preferably closed completely but it is also possible for the shut-off member to be only partly closed so that the flexible line is not clamped completely shut. The only thing that is crucial is that the kinetics of the blood are changed significantly in the flexible line, thus enabling the blood constituent to be determined by the known methods of measurement on the basis of the measurement of transmission, reflection or scattered light.

BRIEF DESCRIPTION OF THE DRAWINGS

The invention will be explained in detail in what follows by reference to the drawings. In the drawings.

DETAILED DESCRIPTION OF THE DRAWINGS

Figure 1:
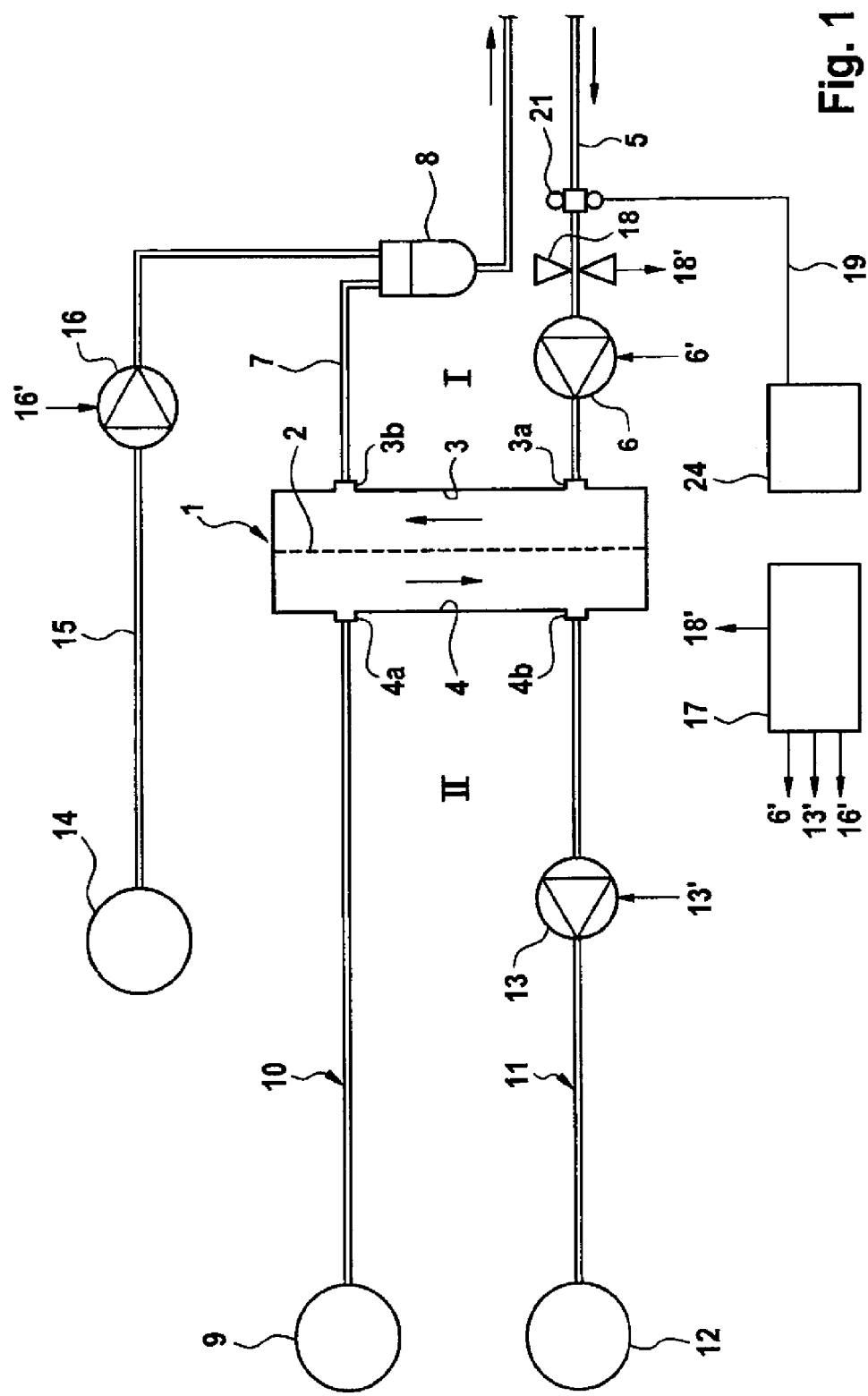
FIG. 1 is a highly simplified schematic view showing the main components of an extra-corporeal blood treating apparatus, together with the arrangement for measuring a blood constituent in blood.

FIG. 1 is a highly simplified schematic view showing those components which are relevant to the invention of an extra-corporeal blood treating apparatus which can be operated both as a hemodialysis apparatus and/or as a hemofiltration apparatus. The extra-corporeal blood treating apparatus is therefore referred to below as a hemodiafiltration apparatus.

The hemodiafiltration apparatus has a dialyzer or filter 1 which is separated by a semi-permeable membrane 2 into a blood chamber 3 and a dialysis-fluid chamber 4. The inlet 3a of the blood chamber is connected to one end of the arterial blood inlet line 5, into which a blood pump 6 is connected, while the outlet 3b of the blood chamber is connected to one end of the venous blood return line 7, into which latter a drip chamber 8 is connected. At the other ends of the arterial and venous blood lines 5, 7 are situated the arterial and venous needles (not shown) for connection to the patient. This part of the fluid system constitutes the extra-corporeal blood circuit I of the hemodiafiltration apparatus. The blood lines 5, 7 are flexible lines, made of a sufficiently transparent material, which are substantially transmissive of light.

The dialysis-fluid system II of the hemodiafiltration apparatus comprises a means 9 for supplying fresh dialysis fluid which is connected, via a likewise transparent dialysis-fluid inlet line 10, to the inlet 4a of the dialysis-fluid chamber 4 of the dialyzer 1 or filter. A transparent dialysis-fluid return line 11 which runs to a discharge 12 leads away from the outlet 4b of the dialysis-fluid chamber 4 of the dialyzer 1 or filter. A dialysis-fluid pump 13 which is arranged in the dialysis-fluid return line 11 is used to pump the dialysis fluid.

As well as this, the hemodiafiltration apparatus also has a substituent source 14 from which a substituent line 15, into which a substituent pump 16 is connected, runs to the venous drip chamber 8. A preset amount of substituent fluid from the substituent source 14 can be fed into the extra-corporeal blood circuit I by the substituent pump 16 if fluid is withdrawn from the blood circuit via the dialyzer 1.

The diafiltration apparatus also comprises a central control and computing unit 17 which is connected via control lines 6', 13', 16' to the blood pump 6, the dialysis-fluid pump 13 and the substituent pump 16. The control and computing unit 17 transmits control commands to the individual components and receives from the said components data on their states of operation, such as, for example, the pumping rates of the pumps.

The arrangement according to the present invention for measuring a blood constituent in blood, which may form an independent unit or may be part of the extra-corporeal blood treating apparatus, will be described below. In the present embodiment the arrangement according to the present invention is part of the extra-corporeal blood treating apparatus. In the present case the arrangement according to the present invention is used to measure the concentration of glucose in the patient's blood, which latter flows into the blood chamber 3 of the dialyzer 1 via the arterial blood line 5. It is however also possible for blood constituents other than glucose to be measured with the arrangement according to the present invention.

The arrangement for measuring glucose has a measuring set-up 21 (only indicated in general in FIG. 1) which is arranged in the portion of the arterial blood line 5 situated upstream of the blood pump 6. Situated in the arterial blood line 5 between the blood pump 6 and the measuring set-up 21 is a shut-off member 18, and in particular an electro-magnetically operable tube clamp, by which the flexible line can be clamped partly or completely shut. The electro-magnetically operable tube clamp 18 is connected to the central control and computing unit 17 by a control line 18'. The measuring set-up 21 is consequently arranged in the arterial blood line 5 upstream of the shut-off member 18.

The arrangement for measuring glucose also has an analyzing unit 24 which is connected to the measuring set-up 21 by a data line 19. The analyzing unit 24 analyses the measurement data from the measuring set-up 21 and determines the concentration of glucose in the blood, which is displayed on a display unit (not shown).

How the measurement data obtained by the measuring set-up is analyzed is not material to the invention. What is crucial though is the fact that the measurement, by the known methods, is possible because the kinetics of the blood are artificially changed not in the patient's finger but in the arterial blood line 5. The methods which are used to measure a blood constituent may for example be those described in WO 2006/006153 A1 or WO 2007/020647 A1, the disclosure of which is hereby explicitly incorporated by reference.

Figure 2:
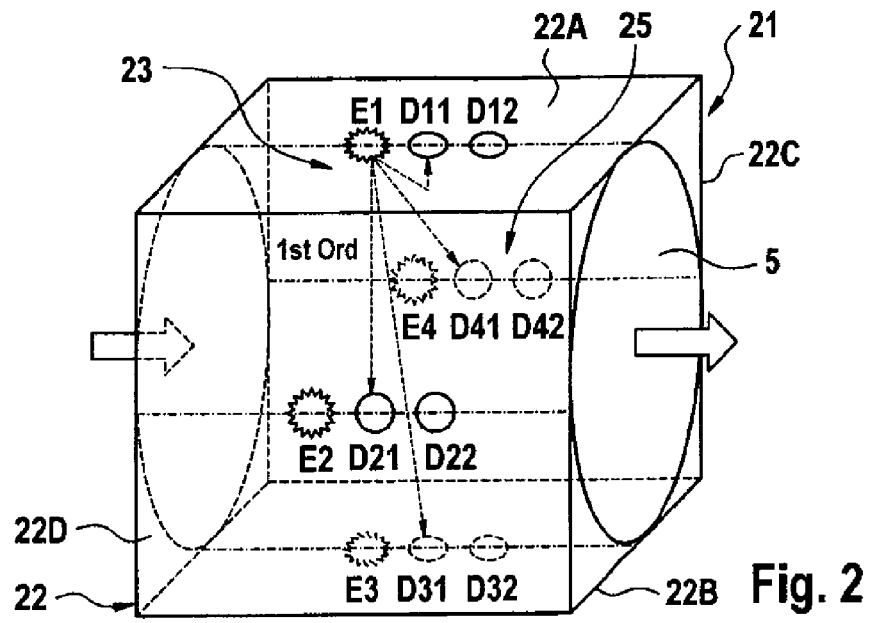
FIG. 2 is a highly simplified schematic view in perspective of the measuring set-up of the arrangement for measuring a blood constituent.
Figure 3:
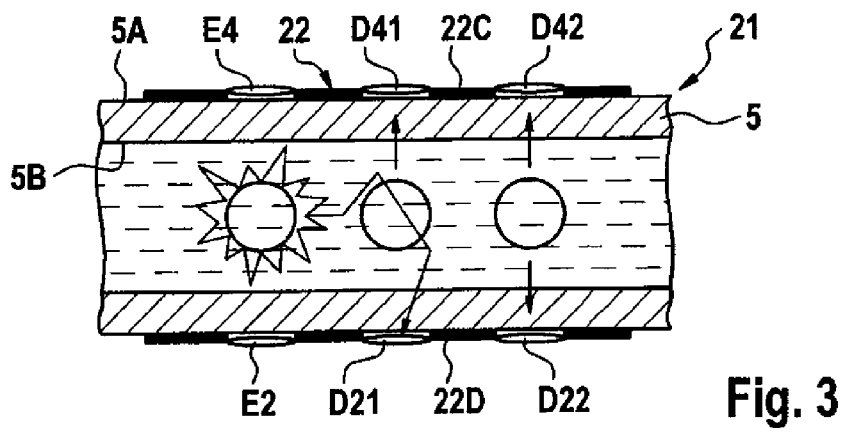
FIG. 3 is a schematic plan view of the measuring set-up of the arrangement for measuring a blood constituent.
Figure 4:
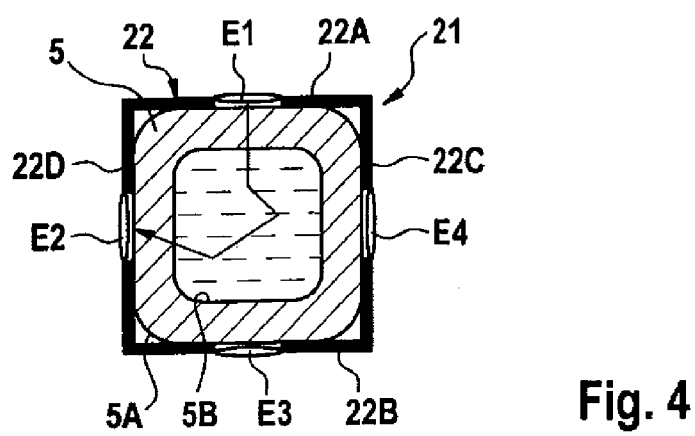
FIG. 4 is a view in section of the measuring set-up.

FIGS. 2 to 4 are enlarged schematic views showing the measuring set-up 21. This is a measuring set-up as described in detail in WO 2004/057313 A1, the disclosure of which is hereby explicitly incorporated by reference.

During measurement, the arterial blood line 5, which is filled with blood, is clamped in the measuring set-up 21. The measuring set-up 21 has for this purpose a clamping-in device 22 having four planar contacting faces 22A, 22B, 22C, 22D, positioned perpendicularly to one another, between which the flexible line 5 can be clamped. The clamping-in device 22 is sized in such a way that the flexible line 5 is able to deform in such a way that it has preferably plane outer and inner surfaces 5A, 5B. As well as this, the measuring set-up 21 also has an emitter 23 for emitting electromagnetic radiation which comprises in particular a plurality of light sources E1, E2, E3, E4, and has a receiver 25 for electromagnetic radiation which comprises in particular a plurality of light detectors D11, D21, D31, D41, D12, D22, D32, D42. Together with the light detectors, the light sources form a measuring device for measuring transmission, a measuring device for measuring scattered light and a measuring device for measuring reflection.

At the top and bottom and along the longitudinal sides, the clamping-in device 22 has respective series of three bores arranged at equal distances from one another in respective ones of which the light sources and light detectors are arranged.

The light sources E1, E2, E3, E4, which are in particular LED's, are, as shown in FIG. 2, arranged in respective bores which are first in the direction of flow, whereas the light detectors D11, D12, D21, D22, D31, D32, D41, D42, which are in particular photodiodes, are arranged in respective bores which are second and third in the direction of flow. It is equally possible for the positions of the light sources and light detectors in the direction of flow to be interchanged.

The LED's E1, E2, E3, E4 emit light of two different wavelengths, preferably $\lambda_1=610$ nm/670 nm and $\lambda_2=805$ nm, which light is detected by the photodiodes D11, D12, D21, D22, D31, D32, D41, D42 as light which passes through the blood-filled flexible line (measurement of transmission), as light which is scattered in the blood-filled flexible line (measurement of scattered light), and as light which is reflected in the blood-filled flexible line (measurement of reflection).

To allow glucose to be measured, artificial blood kinetics are produced at the point of measurement in the blood-filled flexible line. In a preferred embodiment of the invention, the central control and computing unit 17 operates the blood pump 6 in such a way that the blood pump is stopped for a brief interval of time, and in particular for 10 seconds. The blood pump is then put into operation again. As a result the blood kinetics are maximized, as a result of which an improved signal-to-noise ratio is obtained. The red blood corpuscles re-orientate themselves when gravity ceases to act due to the stopping of the blood pump and predominantly settle.

To allow the blood kinetics to be changed, an alternative embodiment makes provision for the central control and computing unit 17 to operate the blood pump 6 in such a way that the pumping rate of the blood pump is increased, from 250 ml/min to 400 ml/min for example, for a brief first interval of time, and is then reduced, to 100 ml/min for example, for a brief second interval of time, the original pumping rate then being set again.

Rather than completely stopping of the blood pump 6, a further alternative embodiment makes provision only for a drastic reduction in the pumping rate of the blood pump. The pumping rate of the blood pump is for example reduced from 250 ml/min to at least 100 ml/min. However, the signal-to-noise ratio which is obtained with this embodiment is not as good as the case where the pump is stopped completely.

In a further alternative embodiment, the central control and computing unit 17 operates the blood pump 6 and the electro-magnetically operable tube clamp 18 in such a way that the blood pump 6 is stopped for a preset brief interval of time and the tube clamp 18 is then closed during the preset brief interval of time, preferably completely or at least partly. As a result the conditions governing flow are changed at the point of measurement in the portion of the arterial blood line 5 which is situated upstream of the tube clamp 18. The blood pump 6 is then put back into operation and the tube clamp 18 is opened again. The closing and opening of the tube clamp may take place continuously during the measurement while the blood pump 6 is stopped, i.e. on the blood pump being stopped, the tube clamp is closed at time $t_{1_n}$ and the tube clamp is opened at time $t_{2_n}$, and so on.

The method of measurement will first be described in a general form. The measuring set-up makes the measurements identified below at the wavelengths $\lambda_1$ and $\lambda_2$ while the blood kinetics are being artificially changed by one of the methods described above.

The measuring set-up 21 measures both the forward scatter/transmission, the back-scatter/reflection and the 90° side scatter. All the measurements are made at the wavelengths $\lambda_1$ and $\lambda_2$.

$FS_{\lambda_1}(t)$—forward scatter/transmission at wavelength $\lambda_1$,
$SS_{\lambda_1}(t)$—90° side scatter at wavelength $\lambda_1$,
$FS_{\lambda_2}(t)$—forward scatter/transmission at wavelength $\lambda_2$,
$SS_{\lambda_2}(t)$—90° side scatter at wavelength $\lambda_2$,
$BS_{\lambda_1}(t)$—back-scatter/reflection at wavelength $\lambda_1$,
$BS_{\lambda_2}(t)$—back-scatter/reflection at wavelength $\lambda_2$,
where $t \in (t_1, t_2)$.

From the measurement data which is obtained for forward scatter, back scatter and side scatter, the analyzing unit 24 calculates at least one of the following intermediate variables:

$$x = S_{\lambda 1}(t)/S_{\lambda 2}(t), S = FS, BS, SS$$

$$y = \frac{dS_{\lambda 1}(t)}{dt} \bigg/ \frac{dS_{\lambda 2}(t)}{dt}, S = FS, BS, SS$$

$$\rightarrow z = \frac{FS_{\lambda 1}(t)/S_{\lambda 1}(t)}{FS_{\lambda 2}(t)/S_{\lambda 2}(t)}, S = BS, SS$$

From the intermediate variables which are calculated, the concentration of glucose in the patient's blood is then determined by the known methods:

$G_{glucose}(t)=g_1(x)$, or
$G_{glucose}(t)=g_2(y)$, or
$G_{glucose}(t)=g_3(z)$.

In contrast to patients whose hemoglobin remains almost constant when glucose is being measured, hemoglobin may vary in dialysis patients in the course of the dialysis treatment due to the ultrafiltration. Variations in hemoglobin of up to 20% are seen in practice. These variations in hemoglobin have a relatively large effect on the accuracy of the measurement of glucose. The arrangement according to the invention for measuring glucose therefore makes provision for appropriate compensation.

During the dialysis treatment, hemoglobin is preferably measured continuously. The measurement of hemoglobin can be made with the same measuring set-up 21 as the measurement of glucose. The measurement of hemoglobin $C_{HB}(t)$ by the known methods however is made on the basis of the measurement of 90° side scatter at a given wavelength, the blood kinetics not being changed.

$C_{HB}(t)=f(SS(t))t\in(t_1, t_2)$.

Hemoglobin $C_{HB}(t)$ having been determined, the value for glucose determined by the method described above is compensated as a function of the hemoglobin.

Appropriate correcting factors, which have been determined empirically and which are stored in a memory belonging to the analyzing unit 24, are provided for this purpose.

An embodiment of the present invention and of the method according to the present invention will be described in detail below.

The measurements were made, with the measuring set-up 21 described above which is known from WO 2004/057313 A1, in laboratory trials using bovine blood which had been temperature controlled to 37° C. The artificial change in the blood kinetics at the point of measurement was produced by stopping the blood pump 6 briefly.

The measurements specified below were made with the measuring set-up 21, the following intermediate variables $y_1(t), y_2(t), y_3(t)$ having been calculated by the analyzing unit 24. Measurement of glucose was performed in this case with only a single wavelength or with two wavelengths.

In the case of measurement with a single wavelength, the intermediate variable to give the correlation with glucose is defined as follows:

$$y_1(t_1)=s(t_1)-s(t_2) \tag{1}$$

where $t_1$=shortly before stopping of the blood pump
$t_2$=shortly after the stopping of the blood pump
s=the signal type may be transmission/forward scatter (FS), side scatter (SS) and reflection/back-scatter (BS).

The relationship which is obtained between the variable and blood glucose concentration, which relationship can be determined by experiment, is as follows:

$C_{glucose}(t_1)=f_1(y_1(t_1))$.

In the case of measurement with two wavelengths, the intermediate variable to give the correlation with glucose is defined as follows:

$$y_2(t_1) = \frac{s_{\lambda 2}(t_1) - s_{\lambda 2}(t_2)}{s_{\lambda 2}(t_2) - s_{\lambda 2}(t_2)} \tag{2}$$

or $$y_3(t_1) = \frac{s_{\lambda 2}(t_1) - s_{\lambda 2}(t_2)}{s_{\lambda 2}(t_2) - s_{\lambda 2}(t_2)}. \tag{3}$$

The relationship which is obtained between the variable and blood glucose concentration, which relationship can be determined by experiment, is as follows:

$C_{glucose}(t_1)=f_2(y_2(t_1))$ or $C_{glucose}(t_1)=f_3(y_3(t_1))$.

Measurement may for example be performed at the different wavelengths: $\lambda_1$=610 nm/670 nm and $\lambda_2$=805 nm.

Glucose content can be determined from the intermediate variables which are determined by means of an empirically performed correlation. To allow the analyzing unit 24 and the measuring set-up 21 to be adjusted, the glucose concentration of human donor blood is artificially changed in a defined way. The intermediate variables which are determined are then correlated with the known glucose content. The mapping of the intermediate variables onto glucose content which is done in this way can be stored in a memory belonging to the analyzing unit 24 as a function to enable the glucose content subsequently to be calculated after each measurement. A linear equation is generally all that is required for this purpose. It is however also possible for the correlation to be stored in the form of a table (a look-up table) in which the intermediate variables and variables for determination are mapped onto one another.

Calibration of the arrangement according to the invention does not need to be individually performed for each arrangement. In practice it is enough for the correlation of intermediate variables and glucose contents to be determined on a reference arrangement. However, to enable the individual manufacturing tolerances, such for example as different distances between the LED's and photodiodes of the measuring set-up 21, to be compensated for, each arrangement for measuring glucose may be individually calibrated in the factory by measuring a reference standard which has defined characteristics. Human blood may be used for this purpose but so too may a replacement fluid and in particular bovine blood.

Figure 5:
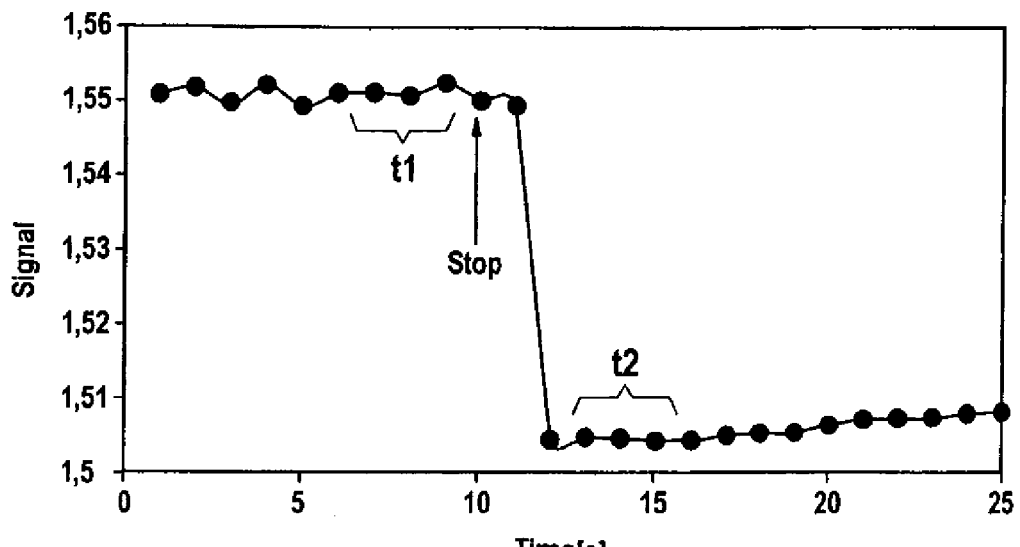
FIG. 5 shows the waveform of the signal which is measured by the measuring set-up when the blood pump is stopped.

When transmission is being measured, FIG. 5 shows the waveform of the signal which is measured with the measuring set-up 21 when the blood pump 6 is stopped. It can be seen that, on the blood pump being stopped, there is an abrupt drop in the signal. To allow the glucose concentration to be determined, the analyzing unit 24 assesses the level of the signal before the blood pump is stopped, during the interval of time $t_1$ for example, and its level after the pump is stopped, during the interval of time $t_2$ for example, in order to determine the intermediate variable.

Figure 6:
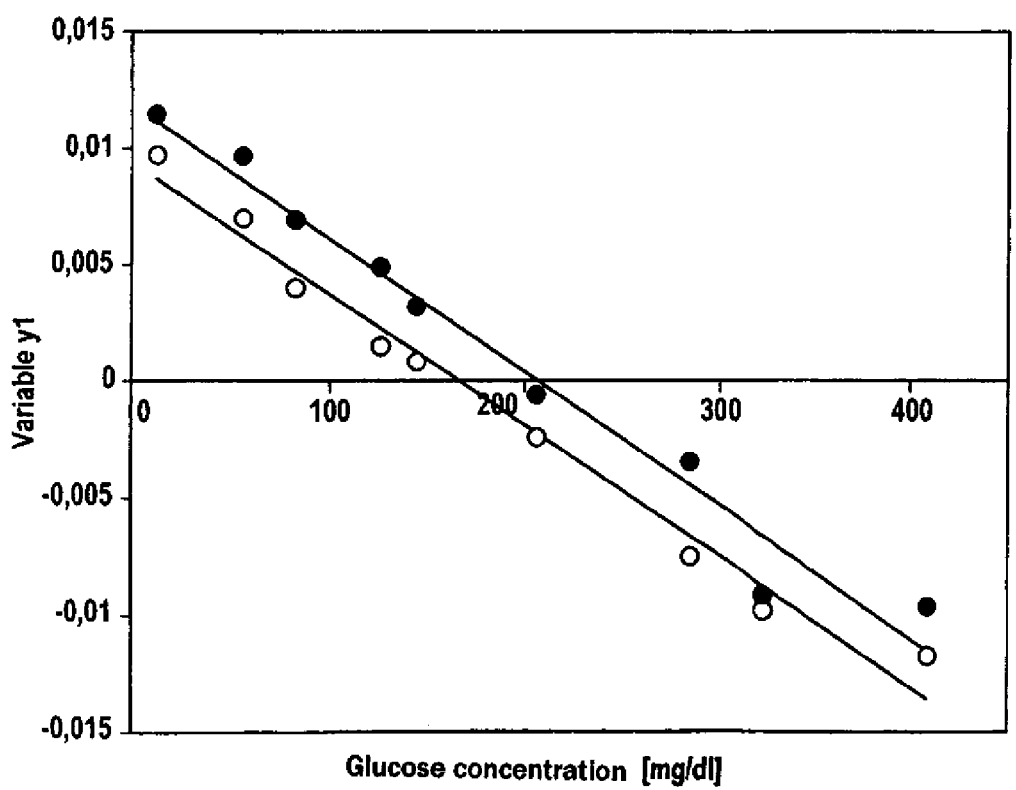
FIG. 6 shows the dependence on glucose concentration of a first intermediate variable $Y_1$ which is determined in the course of measurement, in a measurement of transmission.

FIG. 6 shows the results of the measurements in the case of a measurement of transmission by the measuring set-up 21 at only one wavelength $\lambda=670$ nm and only one wavelength $\lambda=805$ nm (measurements at a single wavelength). The results of the measurement of transmission at the wavelength $\lambda=670$ nm are shown as dots and those at the wavelength $\lambda=805$ nm as circles. The intermediate variable was calculated from equation (1) from the level of the signal during the interval of time $t_1$ shortly before the blood pump was stopped and that during the interval of time $t_2$ immediately after the blood pump was stopped. The blood pump was stopped at a blood flow of 300 ml/min in this case. The correlation coefficient was 0.9735 at a wavelength $\lambda=670$ nm and 0.9805 at $\lambda=805$ nm.

Figure 7:
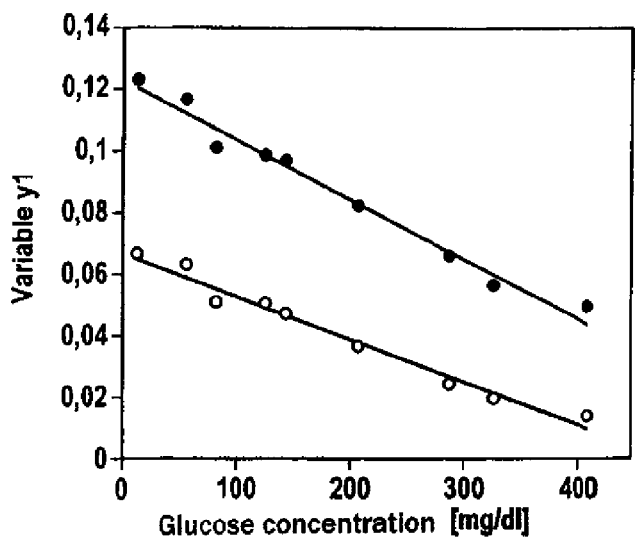
FIG. 7 shows the dependence on glucose concentration of a first intermediate variable $Y_1$ which is determined in the course of measurement, in a measurement of reflection.

FIG. 7 shows the results of the measurements in the case of a measurement of reflection at only one wavelength $\lambda=670$ nm and only one wavelength $\lambda=805$ nm (measurements at a single wavelength). The results of the measurement of reflection at the wavelength $\lambda=670$ nm are shown as dots and those at the wavelength $\lambda=805$ nm as circles. The intermediate variable was calculated from equation (1) from the level of the signal during the interval of time $t_1$ shortly before the blood pump was stopped and that during the interval of time $t_2$ immediately after the blood pump was stopped. The blood pump was stopped at a blood flow of 300 ml/min in this case. The correlation coefficient was 0.9771 at a wavelength $\lambda=670$ nm and 0.9735 at $\lambda=805$ nm.

Figure 8:
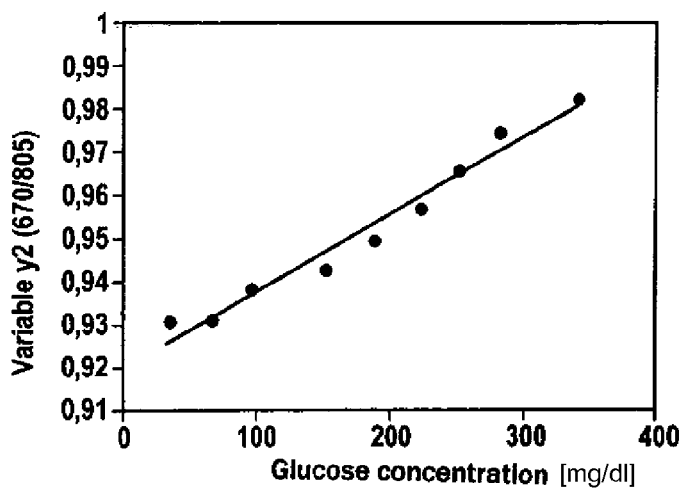
FIG. 8 shows the dependence on glucose concentration of a second intermediate variable $Y_2$ which is determined in the course of measurement, in a measurement of transmission.

FIG. 8 shows the result of the measurements in the case of two measurements of transmission at two wavelengths $\lambda_1=670$ nm and $\lambda_2=805$ nm (measurement at two wavelengths). The intermediate variable was calculated from equation (2) from the level of the signal during the interval of time $t_1$ shortly before the blood pump was stopped and that during the interval of time $t_2$ immediately after the blood pump was stopped, for the first and second wavelengths which were $\lambda_1=670$ nm and $\lambda_2=805$ nm respectively. The blood pump was stopped at a blood flow of 200 ml/min in this case. The correlation coefficient was 0.9713.

Figure 9:
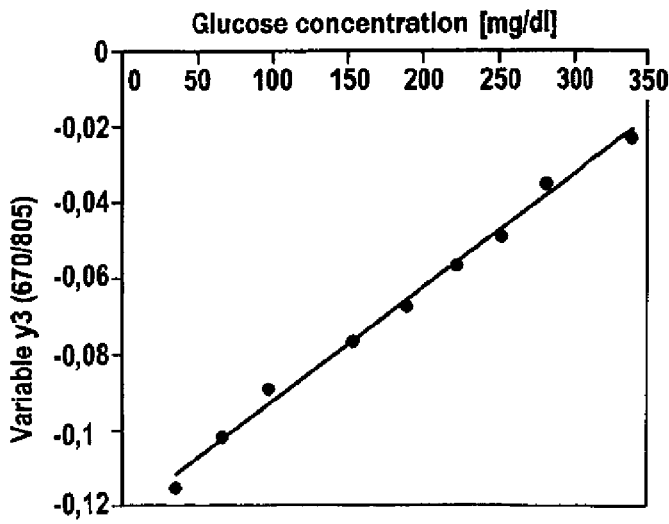
FIG. 9 shows the dependence on glucose concentration of a third intermediate variable $Y_3$ which is determined in the course of measurement, in a measurement of transmission.

FIG. 9 shows the results of the measurements in the case of two measurements of transmission at two wavelengths $\lambda_1=670$ nm and $\lambda_2=805$ nm (measurement at two wavelengths). The intermediate variable was now calculated from equation (3) from the level of the signal during the interval of time $t_1$ shortly before the blood pump was stopped and that during the interval of time $t_2$ immediately after the blood pump was stopped, for the first and second wavelengths which were $\lambda_1=670$ nm and $\lambda_2=805$ nm respectively. The blood pump was stopped at a blood flow of 200 ml/min in this case. The correlation coefficient was 0.9927.

It was found that the determination of glucose content can be performed both with a measurement at a single wavelength and with a measurement at two wavelengths, it being possible for transmission, reflection and/or side scatter to be measured with the measuring set-up. It can be seen that the correlation between the intermediate variables and the variable for determination (glucose concentration) is best when equation (3) is used. In view of the effect of hemoglobin concentration or oxygen saturation, measurement at two different wavelengths is preferred.

What is claimed is:

1. A system for measuring a blood constituent in blood for an extra-corporeal blood treating apparatus, said extra-corporeal apparatus including a system of flexible lines, said flexible lines being substantially transmissive of electromagnetic radiation, wherein the system comprises:
   a measuring set-up comprising:
      an emitter configured to emit electromagnetic radiation which enters one of the flexible lines at a point of measurement, and
      a receiver configured to receive electromagnetic radiation which emerges from the flexible line at the point of measurement,
      wherein the measuring set-up is configured to supply measurement data to an analyzing unit, wherein the measurement data is characteristic of the intensity of the electromagnetic radiation which enters the flexible line at the point of measurement and which emerges from the flexible line at the point of measurement;
   a blood pump arranged in one of the flexible lines and configured to pump blood;
   a shut-off member arranged in one of the flexible lines; and
   a control and computing unit configured to operate the blood pump and the shut-off member, wherein the control and computing unit is configured to stop the blood pump for a preset interval of time and, when the blood pump is stopped, the shut-off member is at least partly closed and then opened, to change the hydrodynamic behavior of the fluid flowing in one of the flexible lines at the point of measurement,
   wherein the analyzing unit is configured to analyze measurement data obtained during the change in hydrodynamic behavior, and is configured to determine the concentration of the blood constituent from the measurement data obtained during the change in hydrodynamic behavior.

2. The system according to claim 1, wherein the emitter is configured to emit electromagnetic radiation of a first wavelength and a second wavelength, said first wavelength and said second wavelength being different from one another.

3. The system according to claim 1, wherein the emitter is configured to emit electromagnetic radiation in different directions which are orthogonal to one another.

4. The system according to claim 1, wherein the receiver is configured to receive electromagnetic radiation from different directions which are orthogonal to one another.

5. The system according to claim 1, wherein the electromagnetic radiation comprises light of a wavelength of between 385 nm and 950 nm.

6. The system according to claim 1, wherein the blood constituent is glucose.

7. An apparatus for extra-corporeal blood treatment comprising:
   a dialyzer or a filter divided by a semi-permeable membrane into a first chamber and a second chamber;
   a system of flexible lines, said flexible lines being transmissive of electromagnetic radiation; and
   a system for measuring a blood constituent in blood for an extra-corporeal blood treating apparatus, wherein the system comprises:
      a measuring set-up comprising:
         an emitter configured to emit electromagnetic radiation which enters one of the flexible lines at a point of measurement, and
         an emitter configured to emit electromagnetic radiation which enters one of the flexible lines at a point of measurement, and a receiver configured to receive electromagnetic radiation which emerges from the flexible line at the point of measurement, wherein the measuring set-up is configured to supply measurement data to an analyzing unit, wherein the measurement data is characteristic of the intensity of the electromagnetic radiation which enters the flexible line at the point of measurement and which emerges from the flexible line at the point of measurement;

a blood pump arranged in one of the flexible lines and configured to pump blood;

a shut-off member arranged in one of the flexible lines; and a control and computing unit configured to operate the blood pump and the shut-off member, wherein the control and computing unit is configured to stop the blood pump for a preset interval of time and, when the blood pump is stopped, the shut-off member is at least partly closed and then opened, to change the hydrodynamic behavior of the fluid flowing in one of the flexible lines at the point of measurement, wherein the analyzing unit is configured to analyze measurement data obtained during the change in hydrodynamic behavior, and is configured to determine the concentration of the blood constituent from the measurement data obtained during the change in hydrodynamic behavior.

8. The apparatus according to claim 7, wherein the system of flexible lines has a blood inlet line that runs to the first chamber of the dialyzer or filter and a blood return line that leads from the first chamber of the dialyzer or filter, wherein when the hydrodynamic behavior of the blood flowing in the blood inlet line is changed, the measuring set-up is arranged on the blood inlet line, and wherein when the hydrodynamic behavior of the blood flowing in the blood return line is changed, the measuring set-up is arranged on the blood return line.

9. The apparatus according to claim 8, wherein the pump is arranged in the blood inlet line, and wherein the apparatus further comprises:

a control and computing unit configured to change the flow rate of the blood in the blood inlet line or the blood return line.

10. The apparatus according to claim 8, wherein the pump is arranged in the blood inlet line and the shut-off member is arranged in the blood inlet line, and the apparatus further comprises:

a control and computing unit configured to change the flow rate of the blood in the blood inlet line or the blood return line.

11. The apparatus according to claim 10, wherein the control and computing unit is configured such that when the blood pump is stopped, the shut-off member is at least partly closed and at least partly opened more than once.

12. The apparatus according to claim 10, wherein the control and computing unit is configured to stop the blood flow on the blood inlet line or the blood outlet line for a preset interval of time and, when the blood pump is stopped, the shut-off member is completely closed.

13. The apparatus according to claim 10, wherein the shut-off member comprises a tube clamp arranged on the blood inlet line.

14. The system according to claim 1, wherein the pump is arranged in the blood inlet line and the shut-off member is arranged in the blood inlet line, and the control and computing unit is configured to change the flow rate of the blood in the blood inlet line or the blood return line.

15. The system according to claim 1, wherein the control and computing unit is configured such that when the blood pump is stopped, the shut-off member is at least partly closed and at least partly opened more than once.

16. The system according to claim 1 wherein the shut-off member comprises a tube clamp arranged on the blood inlet line.

17. The apparatus according to claim 7, wherein the emitter is configured to emit electromagnetic radiation of a first wavelength and a second wavelength, said first wavelength and said second wavelength being different from one another.

18. The apparatus according to claim 7, wherein the emitter is configured to emit electromagnetic radiation in different directions which are orthogonal to one another.

19. The apparatus according to claim 7, wherein the receiver is configured to receive electromagnetic radiation from different directions which are orthogonal to one another.

20. The apparatus according to claim 7, wherein the electromagnetic radiation comprises light of a wavelength of between 385 nm and 950 nm.

21. The apparatus according to claim 7, wherein the blood constituent is glucose.

* * * * *